(12) United States Patent
Hermand

(10) Patent No.: US 6,645,534 B2
(45) Date of Patent: Nov. 11, 2003

(54) PROCESS FOR THE SOLVENT EXTRACTION OF ACTIVE COMPOUNDS FROM CHICORY

(75) Inventor: Olivier Hermand, Haubourdin (FR)

(73) Assignee: Finaler, Orchies (FR)

( * ) Notice: Subject to any disclaimer, the term of this patent is extended or adjusted under 35 U.S.C. 154(b) by 0 days.

(21) Appl. No.: 09/812,629

(22) Filed: Mar. 20, 2001

(65) Prior Publication Data
US 2001/0024643 A1 Sep. 27, 2001

(30) Foreign Application Priority Data
Mar. 22, 2000 (FR) ............................. 00 03669

(51) Int. Cl.$^7$ ............................ A61K 35/78; A61K 7/26
(52) U.S. Cl. ........................ 424/773; 424/725; 424/58
(58) Field of Search ................. 424/725, 773, 424/58

(56) References Cited

U.S. PATENT DOCUMENTS 4,671,962 A * 6/1987 Leroux
6,190,678 B1 * 2/2001 Hasenoehri et al.

FOREIGN PATENT DOCUMENTS

| | | | |
|---|---|---|---|
| EP | 0 126 513 A1 | | 11/1984 |
| JP | 10072333 | * | 3/1998 |
| SU | 1630757 | * | 2/1991 |
| SU | 1658969 | * | 6/1991 |

OTHER PUBLICATIONS

Patel et al. Therapie (Paris). 1983. vol. 38, No. 4, pp. 405–414.*

Grodzinska–Zachwieja et al. Bull. Acad. Scil, Ser. Sci. Biol. 1962. vol. 10, pp. 513–517.*

*Changes in browning characteristics of chicory roots by roasting processes*, Mi–Jung Hong et al., *J. Korean Soc. Food Sci. Nutr.*, 27(4), 591–595, (1998) (translated).

* cited by examiner

*Primary Examiner*—Christopher R. Tate
(74) *Attorney, Agent, or Firm*—Weingarten, Schurgin, Gagnebin & Hayes LLP

(57) ABSTRACT

The present invention relates to a process for the solvent extraction of active compounds from chicory. Characteristically, according to the invention, chicory is macerated in said solvent at a low temperature, preferably of between 0° C. and 6° C., for a period of at least twelve hours; and the maceration liquor is filtered with a cut-off threshold of at least 0.22 μm. The present invention further relates to the use of the extract obtained by the process of the invention for the preparation of an oral hygiene composition and for the preparation of cosmetic products.

27 Claims, No Drawings

PROCESS FOR THE SOLVENT EXTRACTION OF ACTIVE COMPOUNDS FROM CHICORY

The present invention relates to a process for the solvent extraction of active compounds from chicory root and especially roasted chicory root. The present invention further relates to the extract obtained by this process, which has particularly valuable properties, especially in the field of oral hygiene. The present invention further relates to a toothpaste and a mouthwash containing the extract of the invention.

The root of wild chicory, also known as Cichorium Intybus Linn (abbreviated to CIL in the remainder of the present text), has been used since ancient times in the field of foodstuffs and for its medicinal properties.

In the field of foodstuffs, chicory root is often used after roasting. In the pharmaceutical field, on the other hand, it is roots dried in hot air which are almost exclusively used.

In 1983, Patel and Venkatakrishna showed the properties of roasted chicory root extract in the prevention of dental plaque and the treatment of gingivitis. The extract used by these authors is obtained by hot extraction from crude powder of dried and roasted chicory root in the presence of water or ethanol in a Soxhlet extractor.

The resulting extract is in the form of a black viscous liquid. This chicory extract, used in massage, affords a substantial reduction in inflammation of the gums, has antimicrobial properties and proves an effective inhibitor of dental plaque.

The present invention proposes a process for the solvent extraction of active compounds from chicory which differs from the process described above.

Characteristically, in the solvent extraction process of the invention, chicory is macerated in a solvent at a temperature of between 0° C. and 6° C. for a period greater than or equal to 12 hours, and the maceration liquor is filtered with a cut-off threshold of at least 0.22 $\mu$m.

Filtration with such a cut-off threshold makes it possible to obtain a clear and active extract from any chicory maceration liquor, which is not obvious given that the active compounds of chicory have not yet been identified. However, it is not excluded, especially if the clarity is not prohibitive, to carry out the filtration with a higher cut-off threshold or to use other techniques to separate the extract and the solid residues.

It is also possible according to the invention, depending on the amount of solids extracted, to carry out one or more solid-liquid separation steps, optionally by filtration, before carrying out the filtration step on the maceration liquor with a cut-off threshold of at least 0.22 $\mu$m.

Knowing that the solubility (and coefficients of diffusion) of the compounds contained in chicory, for example insulin, increases with temperature, it is therefore totally surprising that it is possible to extract active compounds from chicory root at the temperatures provided by the process of the invention. The low temperatures of the extraction process of the invention also allow good preservation of the resulting extract without the addition of preservative, since there is little development of the bacteria at the extraction temperatures of the process of the invention. Furthermore, the process of the invention avoids all thermal degradation of the chicory which might possibly denature the active compounds.

Likewise, the Applicant has also demonstrated that filtration down to a cut-off threshold of 0.22 $\mu$m affords an extract which comprises all the active compounds and whose color and clarity are optimal for its subsequent use.

According to the invention, the amount of roasted chicory used is such that before maceration the dry matter content of the mixture of solvent plus chicory is at least 5% and preferably 7.4%. In fact, such amounts afford extracts which have or are capable of having the optimal pharmacological properties (antimicrobial and anti-inflammatory efficacy) and physical properties (turbidity, percentage of dry matter, color) for their subsequent use.

The chicory used within the framework of the present invention is not restricted to a specific category of chicory. For example, it can be dried chicory, roasted chicory or even the soluble chicory available commercially. In the case of roasted chicory, this is preferably obtained by a roasting operation whose final temperature does not exceed 170° C., higher roasting temperatures causing undesirable changes such as a lowering of the extractable fraction and the pH, as well as a weak and pungent taste.

According to the invention, the roasted chicory can be in the form of grains, ground grains, powder, liquid or paste. Nevertheless, to optimize the amount of active compounds which can be extracted by the process of the invention, it is preferable to use powdered chicory so as to maximize the contact area between the chicory and the solvent.

The extract can be obtained with a sufficient clarity by filtering the maceration liquor with a cut-off threshold below or equal to 10 $\mu$m.

There are no restrictions on the solvent used in the process of the invention, It can be a protic solvent, for example water or an alcohol. It is preferable to use water for reasons of both cost and safety, which proves advantageous for the subsequent uses of the extract obtained by the process of the invention.

The extract obtained by the process of the present invention can be used especially for the preparation of an oral hygiene composition. It can also be used for the preparation of a cosmetic composition. In fact, the extract obtained by the process of the invention has all the known properties of the chicory extract obtained by hot extraction, namely antimicrobial and anti-inflammatory properties, without having its use-limiting black color.

Preferably, the mouthwash of the invention contains an amount of between 8% and 12% by weight, preferably of 10% or approximately 10% by weight, of the chicory extract obtained by the process of the invention.

Likewise, the toothpaste of the invention contains an amount of between 8% and 12% by weight, preferably of 10% or approximately 10% by weight, of the chicory extract obtained by the process of the invention.

The present invention will be better understood and its characteristics and advantages will be more clearly apparent from the following description and Examples.

EXAMPLE OF THE PREPARATION OF A FIRST CHICORY EXTRACT OF THE INVENTION

The roasted chicory used in this Example has the following physicochemical characteristics:

| | |
|---|---|
| color | 50 to 70 (Neuhaus color test) |
| dry matter measured at 70° C. | >95% |
| mean particle size | 90% < 0.710 mm |
| pH in 10% aqueous solution | between 4.0 and 4.5 | and the following bacteriological characteristics:

| mesophilic aerobic germs | <10/g |
|---|---|
| yeasts | 0/g |
| molds | 0/g |

100 g of the powdered chicory defined above were mixed in a lagged reactor with water purified by osmosis, cooled to 4° C. The mixture is homogenized by gentle stirring for about one minute. The amount of water used is such that the dry matter represents 7.4% by weight of the mixture of water+chicory. The mixture is kept at 4° C. for 24 hours, without stirring. A first filtration is then carried out to remove the suspended matter. This filtration is carried out for example by means of a filter cloth with a cut-off threshold of 10–20 μm. This first filtration can also be effected by centrifugation or by any other known solid-liquid separation technique. This first filtration produces a solid pulp which represents about 18% by volume of the initial mixture and whose dry matter content is 16.5%. The maceration liquor also obtained represents 82% by volume of the initial mixture and has a dry matter content in the order of 6%. This maceration liquor is diluted with water purified by osmosis in order to make it up to the initial volume of water mixed with the chicory. After this dilution, the dry matter content of the maceration liquor is in the vicinity of 4.5%.

A second filtration is then carried out with the principal aim of obtaining a clear maceration liquor. This is done using cellulose plates of the K900, K300 or S80 type, which have mean cut-off thresholds of between 8 and 10 μm, between 4 and 6 μm, and 0.22 μm respectively. Any other analogous technique, such as membrane filtration, can also be used. The filtrate obtained corresponds to the chicory active compound extract of the present invention.

This extract has the following characteristics:

| total dry matter | 4 to 5% |
|---|---|
| pH | 4 to 4.5 |
| ash/dry matter | 4.4 to 5.6% |
| proteins/dry matter | 3.1 to 4.1% |
| coloration (measured at 420 nm) | 1500 to 1700 |
| turbidity (measured at 600 nm) | 0.100 to 0.140 |
| glucose/dry matter | 7.5 to 9.5% |
| fructose/dry matter | 7.0 to 9.0% |
| DP2/dry matter | 14.0 to 16.0% |
| inulin/dry matter | 6 to 9% |

In the case of an extract obtained after centrifugation for the solid-liquid separation and filtration with a cut-off threshold of 0.22 μm, the overall mean value obtained for the coloration, measured at 420 nm, is between 0.800 and 1.700 and the mean value obtained for the turbidity, measured at 600 nm, is between 0.085 and 0.140.

Carrying out the maceration step without stirring makes it possible to influence the material balance and the liquid/solid distribution. In fact, the Applicant has noted that the inulin content of the extract obtained is lower without stirring (below 37%), whereas the free sugar content of the extract is independent of stirring. The results concerning the influence of stirring are collated in Tables I to III annexed to the present description.

The antimicrobial activity of the extract of the invention was also tested.

In vitro Study of the Antibacterial Activity of a Second Example of an Extract of the Invention 200 g of CIL in the dried form are mechanically pulverized and divided up into two batches of 100 grams each. The first batch, called CIC/SEC/ED, is taken up with 400 ml of distilled water and stirred magnetically in a cold chamber at 4° C. overnight. A further 400 ml of distilled water are added to the greatly swollen mixture and aqueous extraction is repeated. After 24 hours, the mixture is filtered and the retained material is washed copiously.

The second batch, called CIC/SEC/ALC, is taken up with 400 ml of absolute ethanol (99%) and stirred magnetically in a cold chamber at 4° C. overnight. The mixture is then filtered and the retained material is washed copiously with pure ethanol. The alcoholic filtrate is evaporated on a Büchi rotary evaporator under vacuum at 50° C. The pasty residue is taken up with 30 ml of distilled water and dialyzed against distilled water, the dialysis being continued for four days with daily renewal of the distilled water used. The extract is then preserved by freezing at −34° C. Two other batches, called CIC/GRI/ED and CIC/GRI/ALC respectively, were prepared from roasted chicory in the manner described above.

Each of the dry extracts frozen in a chill mold is lyophilized. The lyophilization proved a lengthy operation, but no premature or untimely thawing of the samples was observed.

When lyophilization was complete, the amounts of dry matter were measured.

|  | CIC/SEC/ED | CID/GRI/ED | CIC/SEC/ALC | CIC/GRI/ALC |
|---|---|---|---|---|
| WEIGHT (g) | 7.96 | 14.36 | 0.4462 | 0.6742 |
| DRY WEIGHT OF EXTRACT/200 g OF STARTING MATERIAL (%) | 3.98% | 7.18% | 0.22% | 0.33% |

The aqueous extracts (CIC/SEC/ED and CIC/GRI/ED) are taken up with 100 ml of distilled water, whereas the alcoholic extracts are taken up with 10 ml of distilled water. A solution of commercial soluble chicory was also prepared in proportions of 10 g per 100 ml of TGY culture medium. TGY medium is defined as follows:

| trypticase | 30 g |
|---|---|
| yeast extract | 10 g |
| glucose | 27 mM |
| Tris buffer | 100 mM |
| hydrochloric acid qs | pH 7.5 |
| double-distilled water qs | 1000 ml |

The medium of the above formulation is divided up into 25 ml tubes and sterilized in an autoclave.

This TGY medium is used for the culture of Streptococcus mutans IM 2201 and *Bacterionema matruchotii* IM 2219, both originating from the Institut Mérieux collection. The cultures introduced into TGY medium are incubated at 37° for 24 hours.

In a separate procedure, human dental plaque freshly taken from a patient was also cultured in "brain-heart" liquid medium. After 24 h of development, this plaque isolate is subcultured on the medium described above.

Likewise, *Prevotella intermedia* AIP N 161/79 (ex *Bacteroides intermedius*) and *Porphyromonas gingivalis*

ATCC 33277, originating from the Institut Pasteur collection, Paris, and from the American collection, are cultivated under anaerobic conditions for 24 hours and 48 hours at 37° C. in a liquid medium of the following composition:

| | |
|---|---|
| trypticase | 30 g |
| yeast extract | 20 g |
| cysteine | 0.5 g |
| hemin | 5 mg |
| glucose | 180 mM |
| distilled water qs | 1000 ml |

Test culture media were prepared. 25 ml tubes of TGY respectively receive 0.5 ml of aqueous extract of dried chicory (CIC/SEC/ED=0.15% w/v), 0.5 ml of aqueous extract of roasted chicory (CIC/GRI/ED=0.28% w/v), 1 ml of commercial chicory solution (≈0.4% w/v), 0.5 ml of alcoholic extract of roasted chicory (CIC/GRI/ALC=0.09% w/v) and 0.5 ml of alcoholic extract of dried chicory (CIC/SEC/ALC=0.13% w/v). Each culture tube supplemented with aqueous or alcoholic extract contains the equivalent of 1 g or 10 g of CIL, respectively. All these tubes are placed in an autoclave for 30 minutes and stored at 4° C. It should be noted that these concentrations are compatible with the conditions of use of chicory in human nutrition.

1 ml of 24-hour culture medium, either of Streptococcus mutans or of human dental bacterial plaque isolate, is incorporated under sterile conditions into each of the test media described above, to which control tubes devoid of any trace of chicory in any form whatsoever are added.

The activity of the chicory extract is shown by statistical analysis. At times ranging from 0 to 21 h, 3 ml samples are taken from each tube after agitation on a Vortex. Each sample is centrifuged at 500×g for 5 min at 4° C. (these conditions respect the integrity of the bacterial substances). The supernatants are carefully removed and 2 ml of distilled water are added to each residue. The whole is then agitated on a Vortex to redisperse the bacterial cells in the aqueous phase. The turbidity, which reflects the bacterial growth for a given culture, is measured for each sample in a Beckman DU5 spectrophotometer (aspiration device, regulated temperature, wavelength 610 nm).

The outcome of these experiments is that the CIL extracts of the invention perturb bacterial growth during the logarithmic phase. For Streptococcus mutans IM 2209, the most substantial effect manifests itself in the first few hours of growth.

It is the *Bacterionema matruchotii* IM 2219 culture which seems to be the most sensitive to the CIL extracts of the invention. The inhibitory effect is particularly manifest in the second growth phase, between 28 and 48 hours, with all the forms of CIL (aqueous extract of dried chicory, aqueous extract of roasted chicory, alcoholic extract of dried chicory, alcoholic extract of roasted chicory, and commercial chicory).

The Applicant has also demonstrated this same inhibitory effect on cultured human dental bacterial plaque, a slowing-down of the overall growth being evident after eleven hours and being more pronounced with the aqueous extract of roasted chicory. The anaerobic germs tested are also sensitive to the CIL extracts of the invention.

With Prevotella intermedia, this effect is more pronounced with the aqueous extracts but remains significant with all the forms used, including the commercial chicory. The growth of *Porphyromonas gingivalis* is affected to the extent of about 10 to 20%.

It should be noted that the concentrations of the CIL extracts of the invention used in this case are comparable to the levels normally consumed in human nutrition, being equivalent to 1 g of starting material (aqueous extract) or 10 g (alcoholic extract) for 25 ml of culture medium solution.

In conclusion, the CIL extract of the present invention reduces in vitro the growth of the bacterial species most representative of buccal flora. Their growth is slowed down by an average of 10% to 50%, depending on the species, the nature of the extracts and the culture times on liquid medium.

In Vivo Study of the Antibacterial Activity of the First Example of an Extract of the Invention The extract of the invention used for this study is obtained after macerating a mixture of roasted chicory and water purified by osmosis (dry matter content of 7.4% by weight) at 4° C. for 24 hours, without stirring, and filtering the resulting maceration liquor with a cut-off threshold of between 4 μm and 10 μm. The chicory concentration of this extract is such that the dry matter content of said extract is about 4.5% by weight.

This extract was used for the preparation of a mouthwash and a toothpaste each containing about 10% by weight of this extract.

The resulting toothpaste and mouthwash were compared with a toothpaste based on sanguinarine, a mouthwash containing chlorhexidine and two placebos (mouthwash and toothpaste).

Chlorhexidine is a compound commonly employed in periodontology at the present time; it is an effective antiseptic used in numerous fields of medicine because of its low toxicity and its broad antibacterial spectrum.

Sanguinarine is an antiseptic obtained by alcoholic extraction from the plant *Sanguinaria canadensis* originating from northern Canada. It has been observed in vivo that sanguinarine is active against inflammation of the gums. Its use is frequently suggested as a complement to oral hygiene measures in the maintenance phase of periodontal treatment.

The following study was conducted over 45 days on each patient in the period between September 1998 and October 1999 and involved 120 patients satisfying the inclusion criteria. A numbered dossier was assigned to each patient. The patients were aged between 35 and 65 years and presented with adult periodontitis according to the criteria of the American Academy of Parodontology and at least one periodontal pocket larger than 3 mm, confirmed by X-ray and clinical examination (inclusion criteria).

The patients were arbitrarily divided up into six groups:
chicory mouthwash
chicory mouthwash placebo
chicory toothpaste
chicory toothpaste placebo
sanguinarine toothpaste (PERIOGARD®)
0.12% chlorhexidine mouthwash (PAROEX®)
Each group comprises 20 patients.

On day "D0" of the experiment, the patients undergo supragingival scaling so that their initial hygiene conditions are similar. Three indices were recorded on six teeth (16, 12, 24, 36, 32, 44) in the course of the study:
plaque index (Silness and Loe 1964)
gingival index (GI, Loe and Silness 1963)
bleeding index (HR, Mühlemann, modified in 1981)

For the chicory mouthwash group, a decrease is observable between D15 and D45 for the plaque, gingival and bleeding indices. The change in the indices from D15 to D45 is 0.93 to 0.53 (plaque index), 1.01 to 0.52 (gingival index)

and 1.04 to 0.51 (bleeding index). The magnitude of these decreases seems to be comparable to that obtained with the PAROEX® mouthwash.

For the group using the PAROEX® mouthwash, the indices all change favorably, confirming the already proven efficacy of chlorhexidine on the clinical parameters of inflammation and reduction of the accumulation of bacterial plaque. The change in the indices from D15 to D45 is 0.87 to 0.45 (plaque index), 0.96 to 0.58 (gingival index) and 0.97 to 0.62 (bleeding index).

As far as the mouthwash placebo group is concerned, the change in the indices from D15 to D45 is 0.69 to 0.60 (plaque index), 0.79 to 0.66 (gingival index) and 0.97 to 0.71 (bleeding index). The product does not seem to modify the plaque index significantly, has little action on the gingival index despite the effect of brushing, and reduced the bleeding index. Statistical analysis will determine whether these variations are significant.

For the chicory toothpaste group, an overall drop in the three clinical indices was observed. The change in the indices from D15 to D45 is 0.84 to 0.48 (plaque index), 0.90 to 0.46 (gingival index) and 0.97 to 0.51 (bleeding index).

For the PERIOGARD® group, the change in the indices from D15 to D45 is 0.60 to 0.49 (plaque index), 0.65 to 0.61 (gingival index) and 0.83 to 0.68 (bleeding index).

As far as the toothpaste placebo group is concerned, the change in the indices from D15 to D45 is 0.80 to 0.81 (plaque index), 0.85 to 0.73 (gingival index) and 0.81 to 0.90 (bleeding index). The indices observed show small or zero modifications between D15 and D45 at the end of the study. The bleeding index shows a substantial increase, indicating that this is indeed a placebo group.

The statistical analyses performed (Student test) show that, for all the indices, the observed differences are significant, very significant or even highly significant on day D45 in the "chicory mouthwash" group and the "chicory toothpaste" group. Likewise, the variations observed between D15 and D45 are comparable to or even (in the case of toothpaste) greater than those observed with the active products used in the control group.

It should be noted that the taste and color of the extract of the invention used to prepare the mouthwash and toothpaste described above are such that, especially in the proportion indicated previously (10%), the toothpaste and mouthwash obtained both have a pale beige coloration acceptable to the consumer, and a mild taste described by the patients using them as inoffensive or even pleasant. Such results cannot be achieved by using the extract obtained by hot extraction.

Furthermore, no coloration of the users' teeth or buccal, labial or gingival mucosa was noted.

The anti-inflammatory activity of the extract of the invention was also tested in vitro.

In Vitro Study of the Anti-inflammatory Activity of an Example of an Extract of the Invention The extract used for this study corresponds to the extract of the invention obtained in the Example of the preparation of a first chicory extract described above. The main aim of the test is to study the mechanisms of action of chicory on inflammation and the effect on the secretion of interleukin-1 alpha (IL-1$\alpha$), an early inflammation marker.

The in vitro model used consists of cultures of normal human gingival keratocytes. The IL-1$\alpha$ was measured in the keratocyte incubation media by ELISA. The effects of the chicory extract of the invention were compared with those observed in the presence of dexamethasone, used as a reference product. After 24 hours of incubation, the chicory extract tested at concentrations of 0.01 and 0.4% (w/v) showed an effect which can be described as anti-inflammatory on human gingival keratocytes in culture. The observed effects are comparable to or even greater than those obtained in the presence of dexamethasone, a reference pharmacological anti-inflammatory product.

The Applicant further confirmed that IL-1$\alpha$ increased the proteolysis of the extracellular matrix of human gingival fibroblasts in culture. Thus the chicory extract of the invention, which reduces the release of IL-1$\alpha$ from the higher cells of the buccal mucosa (the keratocytes), can be considered to exert an anti-proteolysis protection of the extracellular matrix of the gum in response to an inflammatory reaction.

TABLE I

ANALYTICAL RESULTS:
EXTRACTION OF 5 SAMPLES OF GROUND CHICORY
Extraction takes place
for 24 hours at a temperature of 4° C., without stirring.

|  | pH | Total dry matter | Ash/dry matter | Proteins/ dry matter | Absorption 420 nm | Absorption 600 nm | Glucose %/dry matter | Fructose %/dry matter | DP2 %/dry matter | Inulin %/dry matter |
|---|---|---|---|---|---|---|---|---|---|---|
| 99L059-7 | 4.13 | 4.12 | 5.0 | 4.1 | 1.563 | 0.116 | 7.6 | 8.7 | 14.9 | 8.6 |
| 99L240-7 | 4.03 | 4.08 | 5.10 | 4.1 | 1.707 | 0.118 | 8.7 | 7.8 | 16.0 | 3.5 |
| 2001L089-9 | 4.29 | 4.41 | 4.71 | 4.1 | 1.594 | 0.124 | 8.2 | 7.9 | 15.3 | 8.4 |
| 2001L263-9 | 4.23 | 4.53 | 5.23 | 3.1 | 1.710 | 0.133 | 7.7 | 8.0 | 14.6 | 7.5 |
| 2001L309-9 | 4.22 | 4.39 | 5.6 | 3.2 | 1.632 | 0.125 | 7.8 | 7.0 | 14.9 | 8.2 |
| Mean | 4.18 | 4.31 | 5.12 | 3.7 | 1.641 | 0.123 | 8.0 | 7.88 | 15.2 | 7.24 |
| CV | 2.41% | 4.54% | 6.34% | 13.27% | 4.02% | 4.9% | 5.65% | 7.7% | 3.55% | 29.4% |

NOTES:
The pH values were measured on the dry matter of the product.
The coloration and clarity were measured at 0.25%, based on the dry matter.
The ash was measured at 550° C.
The inulin was assayed after hydrolysis of the liquor with inulinase at pH 4.5 for 30 minutes.

TABLE II

ANALYTICAL RESULTS:
EXTRACTION OF 5 SAMPLES OF GROUND CHICORY
Extraction takes place
for 24 hours at a temperature of 4° C., with vigorous stirring.

|  | pH | Total dry matter | Ash/dry matter | Proteins/dry matter | Absorption 420 nm | Absorption 600 nm | Glucose %/dry matter | Fructose %/dry matter | DP2 %/dry matter | Inulin %/dry matter |
|---|---|---|---|---|---|---|---|---|---|---|
| 99L059-7 | 4.29 | 5.88 | 5.27 | 4.5 | 1.853 | 0.222 | 8.2 | 8.96 | 12.4 | 12.3 |
| 99L240-7 | 3.98 | 5.7 | 5.52 | 3.6 | 2.030 | 0.226 | 7.9 | 8.4 | 13.77 | 8.9 |
| 2001L089-9 | 4.28 | 6.09 | 5.04 | 3.8 | 1.696 | 0.196 | 7.10 | 7.55 | 12.7 | 12.7 |
| 2001L263-9 | 4.44 | 6.23 | 4.97 | 3.7 | 1.787 | 0.208 | 8.2 | 8.2 | 12.7 | 11.2 |
| 2001L309-9 | 4.16 | 5.98 | 4.97 | 2.8 | 1.538 | 0.174 | 7.7 | 9.6 | 13.5 | 11.6 |
| Mean | 4.23 | 5.97 | 5.15 | 3.7 | 1.7808 | 0.205 | 7.9 | 8.6 | 13.01 | 11.34 |
| CV | 4.01% | 3.35% | 4.46% | 16.3% | 10.22% | 10.24% | 5.8% | 9.1% | 4.5% | 13.05% |

NOTES:
The pH values were measured on the dry matter of the product.
The coloration and clarity were measured at 0.25%, based on the dry matter.
The ash was measured at 550° C.
The inulin was assayed after hydrolysis of the liquor with inulinase at pH 4.5 for 30 minutes.

TABLE III

ANALYTICAL RESULTS: EXTRACTION
OF THE GROUND CHICORY IN THE LABORATORY
Study of different filtration membranes

|  | pH | Total dry matter | Ash/dry matter | Proteins/dry matter | Absorption 420 nm | Absorption 600 nm | Glucose %/dry matter | Fructose %/dry matter | DP2 %/dry matter | Inulin %/dry matter |
|---|---|---|---|---|---|---|---|---|---|---|
| K900 | 3.91 | 5.09 | 4.22 | 4.03 | 1.667 | 0.169 | 8.6 | 8.5 | 14.8 | 5.5 |
| K300 | 4.12 | 5.09 | 4.44 | 3.92 | 1.597 | 0.139 | 9.3 | 8.95 | 15.5 | 6.3 |
| S80 | 5.21 | 3.52 | 5.42 | 3.4 | 0.806 | 0.085 | 9.1 | 8.2 | 16.3 | 5.0 |

K900 membrane: cut-off threshold of 8–10 μm
K300 membrane: cut-off threshold of 4–6 μm
S80 membrane: cut-off threshold of 0.22 μm

What is claimed is:

1. A process for preparing a chicory extract having antimicrobial and antiinflammatory activity comprising:
   (a) macerating chicory root in an aqueous or alcohol solvent at a temperature between 0° C. and 6° C., for a period of at least twelve hours, wherein the maceration step produces a maceration liquor;
   (b) filtering said maceration liquor through a filter having a cut-off threshold of at least 0.22 μm to obtain a filtrate of active compounds from chicory; and
   (c) recovering the filtrate.

2. A process according to claim 1 wherein the amount of chicory used is such that the dry matter content of the macerated chicory in step (a) is at least 5%.

3. A process according to claim 1 wherein, prior to the filtration with a cut-off threshold of at least 0.22 μm, a first filtration is carried out with a cut-off threshold of between 10 μm and 20 μm.

4. A process according to claim 3 wherein, after said first filtration, the filtrate is diluted so that the dry matter in said filtrate is equal or approximately equal to 4.5%.

5. A process according to claim 1 wherein said chicory is roasted before maceration.

6. A process according to claim 1 wherein said chicory is in powder form and a homogeneous mixture of the chicory and said solvent is prepared with gentle stirring.

7. A process according to claim 1 wherein in step (a) of macerating chicory, the maceration liquor is kept at said temperature without stirring.

8. A process according to claim 1 wherein the maceration liquor is filtered with a cut-off threshold below or equal to 10 μm.

9. A process according to claim 1 wherein said solvent used is water.

10. A process according to claim 9 wherein said chicory is macerated at a temperature equal or approximately equal to 4° C.

11. A process according to claim 10 wherein said chicory is macerated for a period equal or approximately equal to 24 hours.

12. An oral hygiene composition having pale beige coloration, comprising an effective amount of the chicory extract obtained by the process according to claim 1,
   wherein said composition has coloration having an overall mean value, measured at 420 nm, between 0.800 and 1.700 and turbidity having a mean value, measured at 600 nm, between 0.085 and 0.140.

13. A cosmetic composition having pale beige coloration, comprising an effective amount of the chicory extract obtained by the process according to claim 1,
   wherein said composition has coloration having an overall mean value, measured at 420 nm, between 0.800 and 1.700 and turbidity having a mean value, measured at 600 nm, between 0.085 and 0.140.

14. A mouthwash containing an amount of between 8% and 12% by weight of the chicory extract obtained by the process according to claim 2.

15. A toothpaste containing an amount of between 8% and 12% by weight of the chicory extract obtained by the process according to claim 2.

16. A process according to claim 2 wherein, prior to the filtration with a cut-off threshold of at least 0.22 μm, a first filtration is carried out with a cut-off threshold of between 10 μm and 20 μm.

17. A process according to claim 16 wherein:

after said first filtration, the filtrate is diluted so that the dry matter in said filtrate is equal or approximately equal to 4.5%;

said chicory root is roasted before maceration;

said roasted chicory is in powder form and a homogeneous mixture of the chicory and said solvent is prepared with gentle stirring;

in step (a), the maceration liquor is kept at said temperature without stirring;

in step (b) the maceration liquor is filtered with a cut-off threshold below or equal to 10 μm;

said solvent used is water;

said chicory powder is macerated at a temperature equal or approximately equal to 4° C.; and said chicory powder is macerated for a period equal or approximately equal to 24 hours.

18. An oral hygiene composition having pale beige coloration, comprising an effective amount of the chicory extract obtained by the process according to claim 17, wherein said composition has coloration having an overall mean value, measured at 420 nm, between 0.800 and 1.700 and turbidity having a mean value, measured at 600 nm, between 0.085 and 0.140.

19. A cosmetic composition having pale beige coloration, comprising an effective amount of the chicory extract obtained by the process according to claim 17, wherein said composition has coloration having an overall mean value, measured at 420 mm, between 0.800 and 1.700 and turbidity having a mean value, measured at 600 nm, between 0.085 and 0.140.

20. A mouthwash containing an amount of between 8% and 12% by weight of the chicory extract obtained by the process according to claim 17.

21. A toothpaste containing an amount of between 8% and 12% by weight of the chicory extract obtained by the process according to claim 17.

22. A process according to claim 1 wherein the amount of chicory used is such that the dry matter content of the macerated chicory in step (a) is at least 7.4%.

23. A mouthwash containing approximately 10% by weight of the chicory extract obtained by the process according to claim 2.

24. A toothpaste containing approximately 10% by weight off the chicory extract obtained by the process according to claim 2.

25. A mouthwash containing approximately 10% by weight of the chicory extract obtained by the process according to claim 17.

26. A toothpaste containing approximately 10% by weight of the chicory extract obtained by the process according to claim 17.

27. A process according to claim 1 wherein said chicory root is dried chicory, soluble chicory or dried chicory, wherein said dried chicory is granulated, ground grain, powder, liquid or paste.

* * * * *

UNITED STATES PATENT AND TRADEMARK OFFICE
CERTIFICATE OF CORRECTION

PATENT NO.    : 6,645,534 B2
DATED         : November 11, 2003
INVENTOR(S)   : Olivier Hermand It is certified that error appears in the above-identified patent and that said Letters Patent is hereby corrected as shown below:

Column 4,
Line 15, "Büichi" should read -- Büchi --; and

Column 12,
Line 18, "off" should read -- of --.

Signed and Sealed this

Twenty-seventh Day of July, 2004

JON W. DUDAS
*Acting Director of the United States Patent and Trademark Office*